United States Patent
Duncan et al.

(10) Patent No.: US 10,961,273 B2
(45) Date of Patent: Mar. 30, 2021

(54) N-CARBOXYANHYDRIDE-BASED-SCALE SYNTHESIS OF ELAMIPRETIDE

(71) Applicant: Stealth BioTherapeutics Corp., MC (MC)

(72) Inventors: Scott M. Duncan, Bedford, MA (US); Jan Oudenes, Aurora (CA); Marc W. Andersen, Raleigh, NC (US)

(73) Assignee: Stealth Biotherapeutics Corp., Monte Carlo (MC)

( * ) Notice: Subject to any disclaimer, the term of this patent is extended or adjusted under 35 U.S.C. 154(b) by 61 days.

(21) Appl. No.: 16/325,667

(22) PCT Filed: Aug. 9, 2017

(86) PCT No.: PCT/US2017/046021
§ 371 (c)(1),
(2) Date: Feb. 14, 2019

(87) PCT Pub. No.: WO2018/034901
PCT Pub. Date: Feb. 22, 2018

(65) Prior Publication Data
US 2019/0202861 A1    Jul. 4, 2019

Related U.S. Application Data

(60) Provisional application No. 62/375,579, filed on Aug. 16, 2016.

(51) Int. Cl.
| | | |
|---|---|---|
| *A61K 38/00* | (2006.01) | |
| *C07K 5/11* | (2006.01) | |
| *C07K 5/09* | (2006.01) | |
| *C07K 5/072* | (2006.01) | |
| *C07K 5/065* | (2006.01) | |
| *C07K 5/087* | (2006.01) | |
| *C07K 5/068* | (2006.01) | |
| *C07K 1/06* | (2006.01) | |
| *C07K 1/10* | (2006.01) | |

(52) U.S. Cl.
CPC ............ *C07K 5/1019* (2013.01); *C07K 1/061* (2013.01); *C07K 1/10* (2013.01); *C07K 5/06078* (2013.01); *C07K 5/06086* (2013.01); *C07K 5/06095* (2013.01); *C07K 5/0812* (2013.01); *C07K 5/0817* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 3,846,399 | A | 11/1974 | Hirschmann et al. |
| 3,951,741 | A | 4/1976 | Pfaender et al. |
| 2011/0105722 | A1 | 5/2011 | Callens et al. |
| 2015/0087595 | A1 | 3/2015 | Wilson |

FOREIGN PATENT DOCUMENTS

| | | |
|---|---|---|
| WO | WO-2005/049578 A1 | 6/2005 |
| WO | WO-2015/100376 A1 | 7/2015 |
| WO | WO-2016/001042 A1 | 1/2016 |

OTHER PUBLICATIONS

Extended European Search Report for EP Application No. EP 17841870 dated Feb. 21, 2020.
Fridkin et al., "Peptide Synthesis," Annual Review of Biochemistry, 43(1):419-443 (1974).
Zheng et al., "Synthesis of a Precursor Tripeptide Z-Asp-Val-Tyr-OH of Thymopentin by Chemo-Enzymatic Method," Preparative Biochemistry and Biotechnology, 42(6):520-534 (2012).
Fuller et al., "Urethane-Protected α-amino acid N-carboxyanhydrides and peptide synthesis," Biopolymers, 40(2): 183-254 (1996).
International Preliminary Report on Patentability for International Application No. PCT/US2017/046021 dated Feb. 19, 2019.
International Search Report and Written Opinion for International Application No. PCT/US17/46021 dated Oct. 27, 2017.

*Primary Examiner* — Jeanette M Lieb
(74) *Attorney, Agent, or Firm* — Dana M. Gordon; Foley Hoag LLP

(57) ABSTRACT

Disclosed are methods of making elamipretide (MTP-131), a peptide compound with therapeutic potential for treating various mitochondrial myopathies. The synthesis of the peptide can be achieved via the use of N-carboxyanhydride-modified amino acid residues, which increases the efficiency of the synthetic process and the purity of the peptide product generated.

20 Claims, No Drawings

N-CARBOXYANHYDRIDE-BASED-SCALE SYNTHESIS OF ELAMIPRETIDE

CROSS-REFERENCE TO RELATED APPLICATIONS

This application is the U.S. national stage of International Patent Application No. PCT/US2017/046021, filed Aug. 9, 2017, which claims the benefit of priority to U.S. Provisional Patent Application Ser. No. 62/375,579, filed Aug. 16, 2016.

BACKGROUND OF THE INVENTION

Elamipretide (MTP-131) is a mitochondria-targeting peptide compound with therapeutic potential for treating diseases associated with mitochondrial dysfunction. Elamipretide contains four-amino acid residues, and has been synthesized according to typical linear and convergent solution phase peptide synthesis methods. However, the synthetic route to generate Elamipretide that has been in use to date requires the preparation of various differentially protected peptides, such that certain protecting groups may be removed in order to subject the deprotected compound to peptide coupling, while other protecting groups must remain intact. Thus, there exists a need to develop new synthetic methods to Elamipretide that decrease the need for such iterative protection and deprotection steps.

SUMMARY OF THE INVENTION

Disclosed are convergent and linear methods of synthesizing Elamipretide using N-carboxyanhydride (NCA) based reagents to install amino acid residues. The methods described herein present numerous advantages, particularly in a scaled-up synthesis of Elamipretide, because the NCA-based reagents obviate the need for protecting groups at each step of peptide synthesis, and the NCA-based reagent provides an activated form of the corresponding amino acid, which dispenses with the need to use activating peptide coupling reagents.

DETAILED DESCRIPTION OF THE INVENTION

Elamipretide has been shown to have various therapeutic effects in diseases related to mitochondrial dysfunction. Previous synthetic routes to Elamipretide presented challenges with respect to scale-up due to reliance on protected amino acid reagents and several deprotection steps.

N-carboxyanhydrides (NCAs) have previously been used in solid phase peptide synthesis on a small laboratory scale. Typically, however, NCAs have been regarded as poorly suited for the synthesis of enantiomerically enriched peptides since NCAs are prone to racemization. The present invention is based on the surprising discovery that the use of N-carboxyanhydride analogs of amino acid residues in the synthesis of Elamipretide improves the efficiency of the process and the purity profile of the final product, without the drawbacks typically associated with use of NCAs.

Definitions

The articles "a" and "an" are used herein to refer to one or to more than one (i.e., to at least one) of the grammatical object of the article. By way of example, "an element" means one element or more than one element.

The term "heteroatom" is art-recognized and refers to an atom of any element other than carbon or hydrogen. Illustrative heteroatoms include boron, nitrogen, oxygen, phosphorus, sulfur and selenium.

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, or 10 or fewer (i.e., $C_1$-$C_{10}$). Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "cycloalkyl" means mono- or bicyclic or bridged saturated carbocyclic rings, each having from 3 to 12 carbon atoms. Certain cycloalkyls have from 5-12 carbon atoms in their ring structure, and may have 6-10 carbons in the ring structure.

The term "heterocycloalkyl" as used herein refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 12 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl.

The term "(cycloalkyl)alkyl" as used herein refers to an alkyl group substituted with one or more cycloalkyl groups.

The term "(heterocycloalkyl)alkyl" as used herein refers to an alkyl group substituted with one or more heterocycloalkyl (i.e., heterocyclyl) groups.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s).

The term "alkynyl" as used herein means a straight or branched chain hydrocarbon radical containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

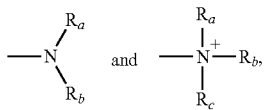

wherein $R_a$, $R_b$, and $R_c$ each independently represent a hydrogen, an alkyl, an alkenyl, —$(CH_2)_x$—$R_d$, or $R_a$ and $R_b$, taken together with the N atom to which they are attached complete a heterocycle having from 4 to 8 atoms in the ring structure; $R_d$ represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally Re) each independently represent a hydrogen, an alkyl, an alkenyl, or —$(CH_2)_x$—$R_d$. In certain embodiments, the term "amino" refers to —$NH_2$.

The term "amido", as used herein, means —NHC(=O)—, wherein the amido group is bound to the parent molecular moiety through the nitrogen. Examples of amido include alkylamido such as $CH_3C(=O)N(H)$— and $CH_3CH_2C(=O)N(H)$—.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "phosphoryl" is a term of art and as used herein may in general be represented by the formula:

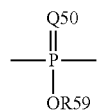

wherein Q50 represents S or O, and R59 represents hydrogen, a lower alkyl or an aryl; for example, —P(O)(OMe)- or —P(O)(OH)$_2$. When used to substitute, e.g., an alkyl, the phosphoryl group of the phosphorylalkyl may be represented by the general formulas:

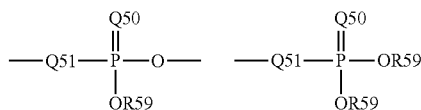

wherein Q50 and R59, each independently, are defined above, and Q51 represents O, S or N; for example, —O—P(O)(OH)OMe or —NH—P(O)(OH)$_2$. When Q50 is S, the phosphoryl moiety is a "phosphorothioate."

The term "aminophosphoryl" as used herein refers to a phosphoryl group substituted with at least one amino group, as defined herein; for example, —P(O)(OH)NMe$_2$.

The term "azide" or "azido", as used herein, means an —$N_3$ group.

The term "carbonyl" as used herein refers to —C(=O)—.

The term "thiocarbonyl" as used herein refers to —C(=S)—.

The term "alkylphosphoryl" as used herein refers to a phosphoryl group substituted with at least one alkyl group, as defined herein; for example, —P(O)(OH)Me.

The term "alkylthio" as used herein refers to alkyl-S—.

The term "carboxy", as used herein, means a —$CO_2H$ group.

The term "aryl" is a term of art and as used herein refers to includes monocyclic, bicyclic and polycyclic aromatic hydrocarbon groups, for example, benzene, naphthalene, anthracene, and pyrene. The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. In certain embodiments, aryl refers to a 5-10 membered ring. Alternatively, the term "aryl" refers to a phenyl group.

The term "heteroaryl" is a term of art and as used herein refers to a monocyclic, bicyclic, and polycyclic aromatic group having 3 to 12 total atoms including one or more heteroatoms such as nitrogen, oxygen, or sulfur in the ring structure, for example, azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls.

The term "aralkyl" or "arylalkyl" is a term of art and as used herein refers to an alkyl group substituted with an aryl group, wherein the moiety is appended to the parent molecule through the alkyl group.

The term "heteroaralkyl" or "heteroarylalkyl" is a term of art and as used herein refers to an alkyl group substituted with a heteroaryl group, appended to the parent molecular moiety through the alkyl group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein. Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2=CH-CH_2-O-$) and vinyloxy (i.e., $CH_2=CH-O-$).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "cyano" is a term of art and as used herein refers to —CN.

The term "halo" is a term of art and as used herein refers to —F, —Cl, —Br, or —I.

The term "haloalkyl" as used herein refers to an alkyl group, as defined herein, wherein some or all of the hydrogens are replaced with halogen atoms.

The term "hydroxy" is a term of art and as used herein refers to —OH.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "silyl", as used herein, includes hydrocarbyl derivatives of the silyl ($H_3Si$—) group (i.e., (hydrocarbyl)$_3$Si—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethyl silyl)ethoxy]methyl (SEM).

The term "silyloxy", as used herein, means a silyl group, as defined herein, is appended to the parent molecule through an oxygen atom.

Certain compounds made by methods of the present invention may exist in particular geometric or stereoisomeric forms. In addition, compounds of the present invention may also be optically active. The present invention contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound made by methods of the present invention is desired, it may be prepared by using an enantiomerically enriched reactant comprising an amino acid residue (e.g., a naturally occurring amino acid residue). Alternatively, the enantiomerically enriched reactants can be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention. An "amino protecting group" means a protecting group that protects an —NH—, —NH$_2$, or —N(R)H moiety, wherein R can be any hydrocarbyl or other substituent. Exemplary amino protecting groups include those that form carbamates such as 9-fluorenylmethyloxycarbonyl (Fmoc), tertbutyloxycarbonyl (Boc), methyloxycarbonyl, and benzyloxycarbonyl (Cbz); amides such as benzoyl (Bz); and N-sulfonyl derivatives such as N-toluenesulfonamide ("tosyl"; Ts) or methanesulfonamide (Ms).

Two protecting groups may be referred to as "orthogonal" when a set of reaction conditions sufficient to deprotect one protecting group is insufficient to deprotect a second protecting group. In other words, in some reaction conditions, one protecting group is cleaved while an orthogonal protecting group (or an orthogonally protected moiety) remains intact. Exemplary pairs of orthogonal protecting groups include, but are not limited to, benzyl (Bn) and tert-butyloxycarbonyl (Boc); benzyl (Bn) and fluorenylmethylenoxy group (Fmoc); and tert-butyl and Fmoc.

For purposes of the invention, the chemical elements are identified in accordance with the Periodic Table of the Elements, CAS version, Handbook of Chemistry and Physics, 67th Ed., 1986-87, inside cover.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

Salts of the compounds made by the methods of the invention include salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids.

As used herein, a protic solvent is a solvent that has a hydrogen atom bound to an oxygen (as in a hydroxyl group) or a nitrogen (as in an amine group). In general terms, any solvent that contains labile H$^+$ is called a protic solvent. The molecules of such solvents readily donate protons (H$^+$) to reagents. In contrast, an aprotic solvent is a solvent that does not have a hydrogen atom bound to an oxygen (as in a hydroxyl group) or a nitrogen (as in an amine group), and it cannot donate hydrogen.

As used herein, a polar protic solvent is a protic solvent that will dissolve many salts. In general, these solvents have high dielectric constants and high polarity. Non-limiting examples of polar protic solvents include acetic acid, ammonia, ethanol, formic acid, isopropanol, methanol, n-butanol, nitromethane, n-propanol, t-butanol, and water.

As used herein, a polar aprotic solvent is a solvent that will dissolve many salts, but lacks an acidic hydrogen; these solvents generally have intermediate to high dielectric constants and polarity. Non-limiting examples of polar aprotic solvents include acetone, acetonitrile, dichloromethane (DCM), dimethyl sulfoxide (DMSO), ethyl acetate, hexamethylphosphoric triamide (HMPT), N,N-dimethylformamide (DMF), and tetrahydrofuran (THF).

As used herein, a nonpolar aprotic solvent is a solvent that will dissolve many salts, but lacks an acidic hydrogen; these solvents generally have low dielectric constants and polarity. Non-limiting examples of nonpolar aprotic solvents include benzene, chloroform, cyclohexane, diethyl ether, hexane, pentane, and toluene.

The nomenclature used to define the peptides is that typically used in the art wherein the amino group at the N-terminus appears to the left and the carboxyl group at the C-terminus appears to the right.

As used herein, the term "amino acid" includes both a naturally occurring amino acid and a non-natural amino acid. The term "amino acid," unless otherwise indicated, includes both isolated amino acid molecules (i.e. molecules that include both, an amino-attached hydrogen and a carbonyl carbon-attached hydroxyl) and residues of amino acids (i.e. molecules in which either one or both an amino-attached hydrogen or a carbonyl carbon-attached hydroxyl are removed). The amino group can be alpha-amino group, beta-amino group, etc. For example, the term "amino acid alanine" can refer either to an isolated alanine H-Ala-OH or to any one of the alanine residues H-Ala-, -Ala-OH, or -Ala-. Unless otherwise indicated, all amino acids found in the compounds described herein can be either in D or L configuration. An amino acid that is in D configuration may be written such that "D" precedes the amino acid abbreviation. For example, "D-Arg" represents arginine in the D configuration. The term "amino acid" includes salts thereof, including pharmaceutically acceptable salts. Any amino acid can be protected or unprotected. Protecting groups can be attached to an amino group (for example alpha-amino group), the backbone carboxyl group, or any functionality of the side chain. As an example, phenylalanine protected by a benzyloxycarbonyl group (Z) on the alpha-amino group would be represented as Z-Phe-OH.

With the exception of the N-terminal amino acid, all abbreviations of amino acids (for example, Phe) in this disclosure stand for the structure of —NH—C(R)(R')—CO—, wherein R and R' each is, independently, hydrogen or the side chain of an amino acid (e.g., R=benzyl and R'=H for Phe). Accordingly, phenylalanine is H-Phe-OH. The designation "OH" for these amino acids, or for peptides (e.g., Lys-Val-Leu-OH) indicates that the C-terminus is the free acid. The designation "NH$_2$" in, for example, Lys-Val-Leu-NH$_2$ indicates that the C-terminus of the protected peptide fragment is amidated. Further, certain R and R', separately, or in combination as a ring structure, can include functional groups that require protection during the liquid phase synthesis.

Where the amino acid has isomeric forms, it is the L form of the amino acid that is represented unless otherwise explicitly indicated as D form, for example, D-Arg.

In certain embodiments, the amino protecting groups on the amino acid residues include 9-fluorenylmethyloxycarbonyl group (Fmoc) and t-butyloxycarbonyl (Boc). The Fmoc group is removed from the amino terminus with base while the Boc group is removed with acid. In alternative embodiments, the amino protecting group may be formyl, acrylyl (Acr), benzoyl (Bz), acetyl (Ac), trifluoroacetyl, substituted or unsubstituted groups of aralkyloxycarbonyl type, such as the benzyloxycarbonyl (Z), p-chlorobenzyloxycarbonyl, p-bromobenzyloxycarbonyl, p-nitrobenzyloxycarbonyl, p-methoxybenzyloxycarbonyl, benzhydryloxycarbonyl, 2(p-biphenylyl)isopropyloxycarbonyl, 2-(3,5-dimethoxyphenyl)isopropyloxycarbonyl, p-phenylazobenzyloxycarbonyl, triphenylphosphonoethyloxycarbonyl or 9-fluorenylmethyloxycarbonyl group (Fmoc), substituted or unsubstituted groups of alkyloxycarbonyl type, such as the tert-butyloxycarbonyl (Boc), tert-amyloxycarbonyl, diisopropylmethyloxycarbonyl, isopropyloxycarbonyl, ethyloxycarbonyl, allyloxycarbonyl, 2 methyl sulphonylethyloxycarbonyl or 2,2,2-trichloroethyloxycarbonyl group, groups of cycloalkyloxycarbonyl type, such as the cyclopentyloxycarbonyl, cyclohexyloxycarbonyl, adamantyloxycarbonyl or isobornyloxycarbonyl group, and groups containing a hetero atom, such as the benzenesulphonyl, p-toluenesulphonyl, mesitylenesulphonyl, methoxytrimethylphenylsulphonyl, 2-nitrobenzenesulfonyl, 2-nitrobenzenesulfenyl, 4-nitrobenzenesulfonyl or 4-nitrobenzenesulfenyl group.

Many amino acids bear reactive functional groups in the side chain. In certain embodiments, such functional groups are protected in order to prevent the functional groups from reacting with the incoming amino acid. The protecting groups used with these functional groups must be stable to the conditions of peptide synthesis, but may be removed before, after, or concomitantly with peptide bond formation.

As used herein, the term "peptide" refers to two or more amino acids covalently linked by at least one amide bond (i.e. a bond between an amino group of one amino acid and a carboxyl group of another amino acid selected from the amino acids of the peptide fragment). The term "peptide" includes salts thereof, including pharmaceutically acceptable salts.

Peptide Synthesis

The present invention provides methods of synthesizing Elamipretide using NCA-based reagents. Elamipretide may be synthesized by convergent peptide synthesis; e.g., a 2+2 peptide synthesis represented generally by Scheme 1. Protecting groups $PG^1$-$PG^4$ are defined herein.

Scheme 1: Convergent Peptide Synthesis

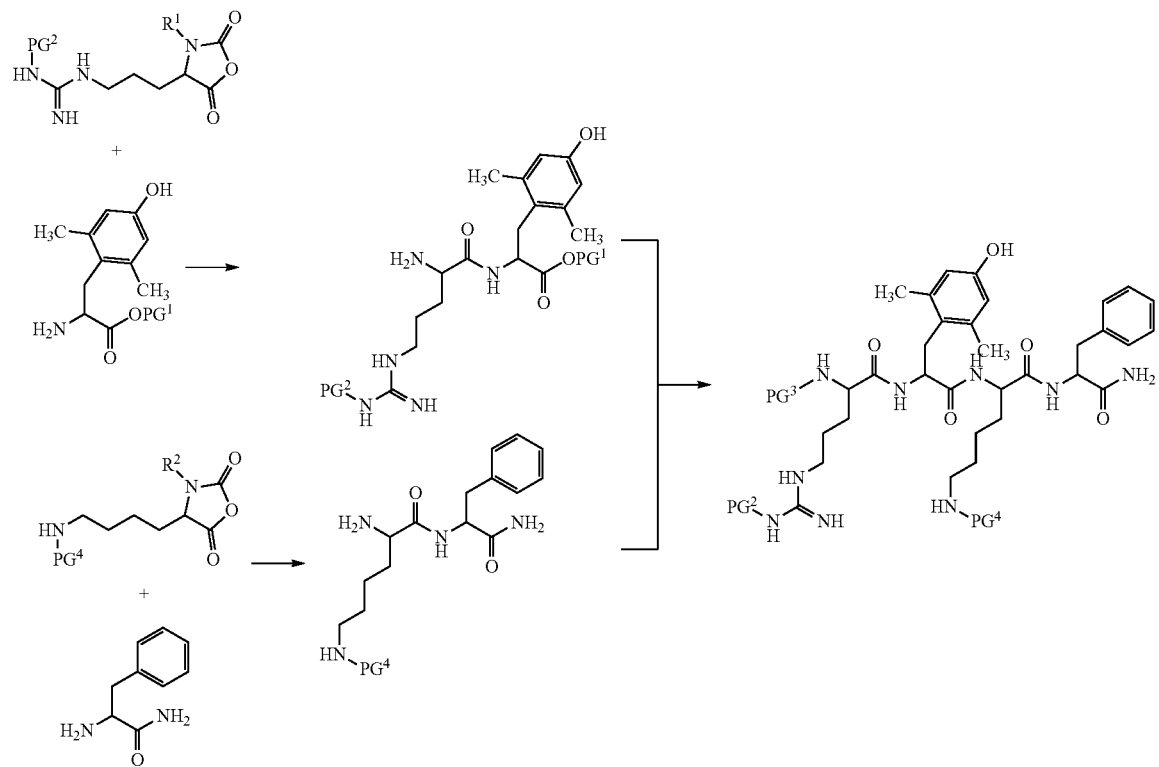

Accordingly, in certain embodiments, the invention provides a method of preparing compound 1, or a salt thereof, comprising:
combining compound 1a and compound 1b under conditions sufficient to produce compound 1, wherein:
compound 1 is represented by:

(compound 1)

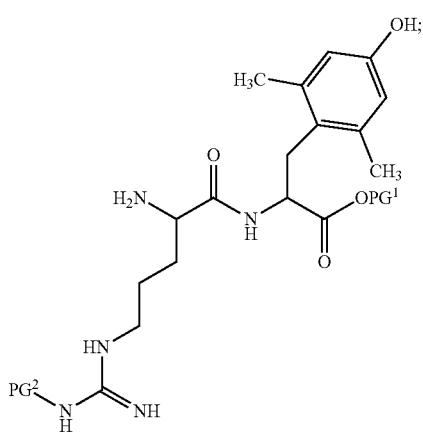

compound 1a is represented by:

(compound 1a)

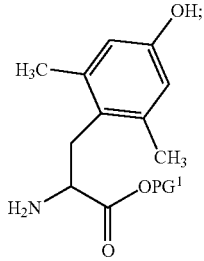

compound 1b is represented by:

(compound 1b)

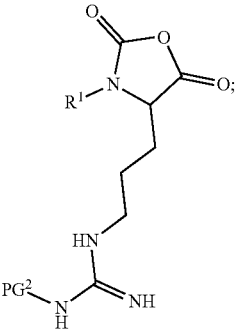

$PG^1$ represents alkyl, aryl, aralkyl, heteroaryl, heteroaralkyl, cycloalkyl, (cycloalkyl)alkyl, heterocycloalkyl, or (heterocycloalkyl)alkyl;
$PG^2$ represents H or an amino protecting group; and
$R^1$ represents H, alkyl, —C(O)O-alkyl, —C(O)O-aryl, —C(O)O-aralkyl, —C(O)O— heteroaryl, —C(O)O-heteroaralkyl, or aralkyl.

In certain embodiments, $PG^1$ represents aralkyl or alkyl. For example, $PG^1$ may represent —CH$_2$Ph.

In certain embodiments, $PG^2$ represents an amino protecting group. Alternatively, $PG^2$ may represent H.

In certain preferred embodiments, $R^1$ represents H.

In certain embodiments, the method further comprises combining compound 1 with an amino protecting reagent represented by $PG^3$-X, thereby forming compound 1c, wherein:
compound 1c is represented by:

(compound 1c)

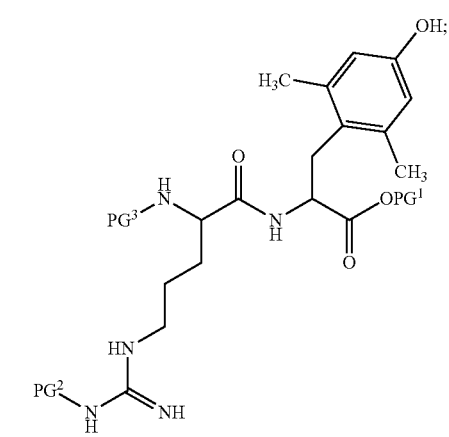

$PG^3$ represents an amino protecting group; and
X represents a leaving group.

In certain embodiments, $PG^3$ is fluorenylmethyloxycarbonyl (Fmoc), tert-butyloxycarbonyl (Boc), benzoyl (Bz), tosyl (Ts), or, if $PG^2$ is an amino protecting group, a protecting group that can be removed under conditions that will not remove $PG^2$ (i.e., $PG^3$ and $PG^2$ are "orthogonal" protecting groups); and X is chloride.

In certain embodiments, the method further comprises combining compound 1c and a deprotection reagent under conditions sufficient to form compound 1d, wherein:
compound 1d is represented by:

(compound 1d)

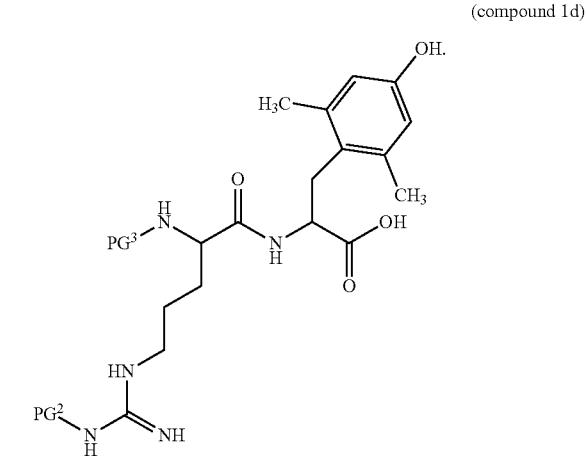

In certain such embodiments, $PG^1$ represents —CH$_2$Ph and the deprotection reagent is H$_2$ and Pd/C.

In certain embodiments, the method further comprises combining compound 1d and compound 2 under conditions sufficient to produce compound 10, wherein:
compound 10 is represented by:

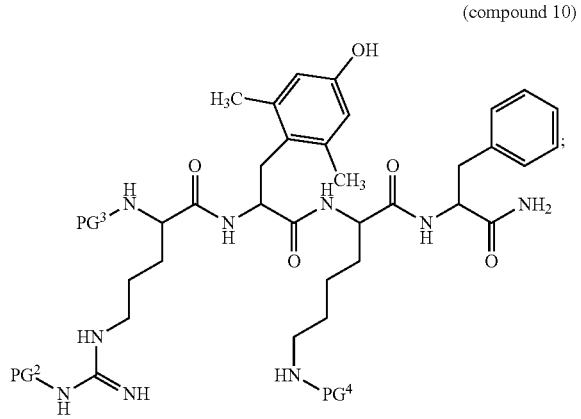

(compound 10)

compound 2 is represented by:

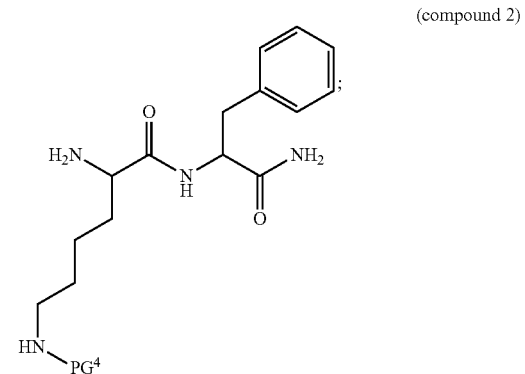

(compound 2)

and
PG$^4$ represents an amino protecting group.

In certain embodiments, the conditions sufficient to produce compound 10 comprise a peptide coupling reagent. Peptide coupling reagents that may be used in the methods described herein are typically carbodiimide reagents. Examples of carbodiimide reagents include, but are not limited to, N,N'-dicyclohexylcarbodiimide (DCC), 1-(3-dimethylaminopropyl)-3-ethylcarbodiimide (EDC), N-cyclohexyl-N'-isopropylcarbodiimide (CIC), N,N'-diisopropylcarbodiimide (DIC), N-tert-butyl-N'-methylcarbodiimide (BMC), N-tert-butyl-N'-ethylcarbodiimide (BEC), bis[[4-(2,2-dimethyl-1,3-dioxolyl)]-methyl]carbodiimide (BDDC), and N,N-dicyclopentylcarbodiimide. In certain preferred embodiments, the peptide coupling reagent is propane phosphonic acid anhydride, N,N'-di(isopropyl)carbodiimide, N,N'-di(cyclohexyl)carbodiimide, 1-ethyl-3-(3-dimethylaminopropyl)carbodiimide, or ethyl 2-cyano-2-(hydroxyimino)acetate.

In certain embodiments, PG$^4$ represents —C(O)O-alkyl, —C(O)O-aryl, —C(O)O— aralkyl, —C(O)O-heteroaryl, —C(O)O-heteroaralkyl, or aralkyl. In certain preferred embodiments, PG$^4$ represents —C(O)O-aralkyl.

In certain embodiments, the method further comprises making the NCA compound 1b by combining compound 1e and a phosgene equivalent reagent under conditions sufficient to produce compound 1b, wherein:
compound 1e is represented by:

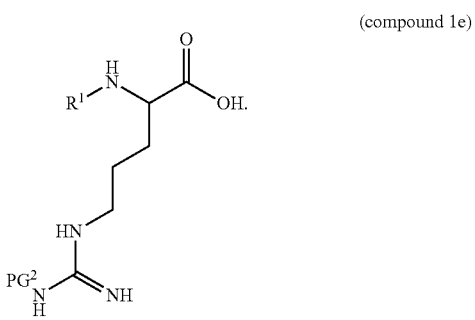

(compound 1e)

In certain embodiments, the phosgene equivalent reagent is selected from the group consisting of phosgene, diphosgene, triphosgene, carbonyl diimidazole, and disuccinimidyl carbonate.

In certain embodiments, the method further comprises combining compound 2a and compound 2b under conditions sufficient to produce compound 2, wherein:
compound 2a is represented by:

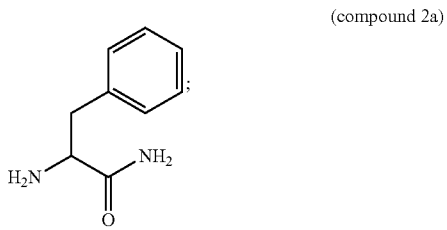 [SMILES: NC(=O)C(N)Cc1ccccc1]

(compound 2a)

compound 2b is represented by:

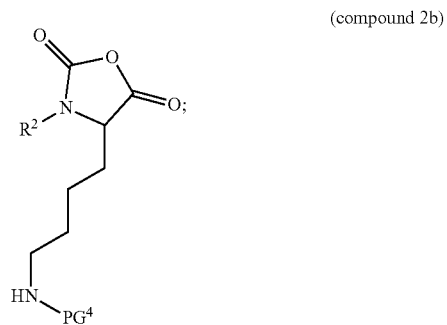

(compound 2b)

and
R$^2$ represents H, alkyl, —C(O)O-alkyl, —C(O)O-aryl, —C(O)O-aralkyl, —C(O)O— heteroaryl, —C(O)O-heteroaralkyl, or aralkyl.

In certain embodiments, R$^2$ is H.

In certain embodiments, the method further comprises combining compound 2c and a phosgene equivalent reagent under conditions sufficient to produce compound 2b, wherein:

compound 2c is represented by:

(compound 2c)

[Structure of compound 2c: R²-NH-CH(COOH)-(CH₂)₄-NH-PG⁴]

In certain embodiments, the phosgene equivalent reagent is selected from the group consisting of phosgene, diphosgene, triphosgene, carbonyl diimidazole, and disuccinimidyl carbonate.

In some embodiments, compound 1 has the following structure:

[Structure of compound 1]

In some embodiments, compound 2 has the following structure:

[Structure of compound 2]

In some embodiments, compound 10 has the following structure:

In other embodiments, the present invention provides a method of preparing compound 2, or a salt thereof, comprising:
combining compound 2a and compound 2b under conditions sufficient to produce compound 2, wherein:
compound 2 is represented by:

(compound 2)

[Structure of compound 2]

compound 2a is represented by:

(compound 2a)

[Structure of compound 2a: H₂N-CH(CH₂Ph)-C(O)-NH₂]

compound 2b is represented by:

(compound 2b)

[Structure of compound 2b: oxazolidine-2,5-dione with R² and (CH₂)₄-NH-PG⁴ substituents]

PG⁴ represents an amino protecting group; and

R² represents H, alkyl, —C(O)O-alkyl, —C(O)O-aryl, —C(O)O-aralkyl, —C(O)O— heteroaryl, —C(O)O-heteroaralkyl, or aralkyl.

In certain embodiments, R² represents H.

In certain embodiments, PG⁴ represents benzyloxycarbonyl (Cbz).

In certain embodiments, the method further comprises combining compound 2c and a phosgene equivalent reagent under conditions sufficient to produce compound 2b, wherein:

compound 2c is represented by:

(compound 2c)

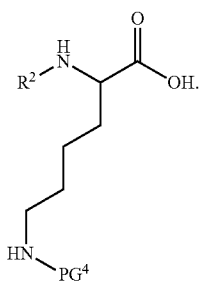

In certain embodiments, the phosgene equivalent reagent is selected from the group consisting of phosgene, diphosgene, triphosgene, carbonyl diimidazole, and disuccinimidyl carbonate.

In some embodiments, the method further comprises comprising combining compound 2 and compound 1d under conditions sufficient to produce compound 10, wherein:

compound 10 is represented by:

(compound 10)

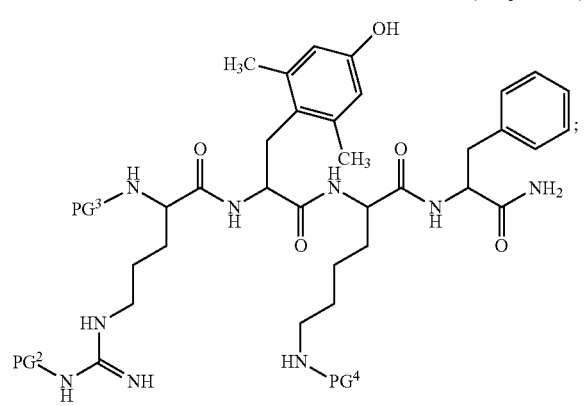

compound 1d is represented by:

(compound 1d)

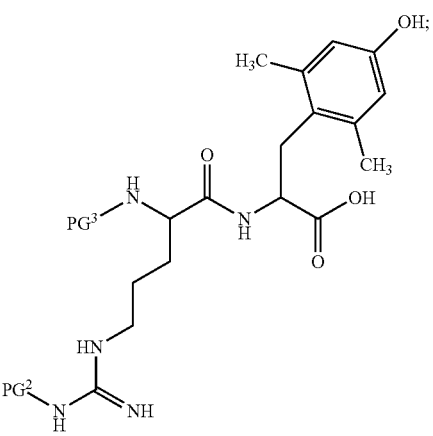

PG² represents H or an amino protecting group; and
PG³ represents an amino protecting group.

In some embodiments, PG² represents an amino protecting group. Alternatively, PG² may represent H.

In certain embodiments, PG³ is fluorenylmethyloxycarbonyl (Fmoc), tert-butyloxycarbonyl (Boc), benzoyl (Bz), tosyl (Ts)), or, if PG² is an amino protecting group, a protecting group that can be removed under conditions that will not remove PG² (i.e., PG³ and PG² are "orthogonal" protecting groups).

In certain embodiments, the conditions sufficient to produce compound 10 comprise a peptide coupling reagent. Peptide coupling reagents that may be used in the methods described herein are typically carbodiimide reagents. Examples of carbodiimide reagents include, but are not limited to, N,N'-dicyclohexylcarbodiimide (DCC), 1-(3-dimethylaminopropyl)-3-ethylcarbodiimide (EDC), N-cyclohexyl-N'-isopropylcarbodiimide (CIC), N,N'-diisopropylcarbodiimide (DIC), N-tert-butyl-N'-methylcarbodiimide (BMC), N-tert-butyl-N'-ethylcarbodiimide (BEC), bis[[4-(2,2-dimethyl-1,3-dioxolyl)]-methyl]carbodiimide (BDDC), and N,N-dicyclopentylcarbodiimide. In certain preferred embodiments, the peptide coupling reagent is propane phosphonic acid anhydride, N,N'-di(isopropyl)carbodiimide, N,N'-di(cyclohexyl)carbodiimide, 1-ethyl-3-(3-dimethylaminopropyl)carbodiimide, or ethyl 2-cyano-2-(hydroxyimino)acetate.

In certain embodiments, compound 2 has the following structure:

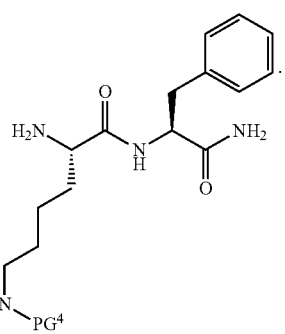

In certain embodiments, compound 1d has the following structure:

19

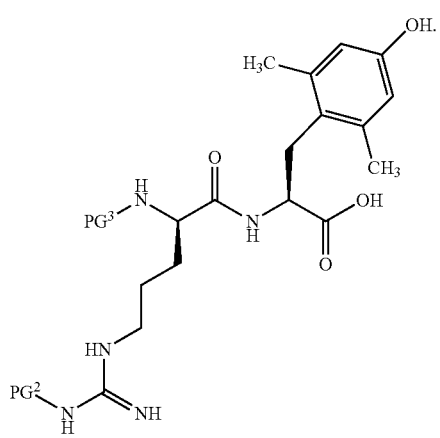

In certain embodiments, compound 10 has the following structure:

20

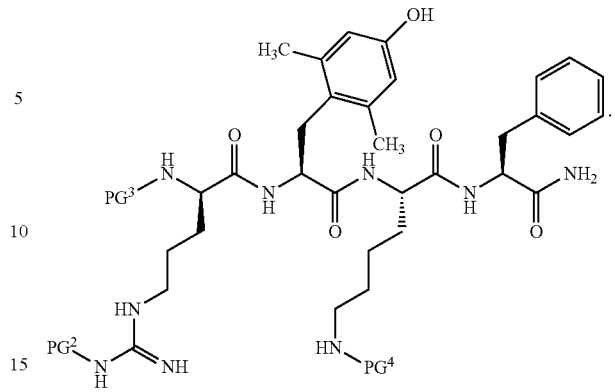

Elamipretide may also be synthesized via a C-to-N linear convergent peptide synthesis, e.g., represented generally by Scheme 2. In such a C-to-N linear peptide synthesis, an NCA reagent is used for each amino acid installation. Protecting groups $PG^1$-$PG^4$ are defined herein.

Scheme 2: C-to-N Linear Peptide Synthesis

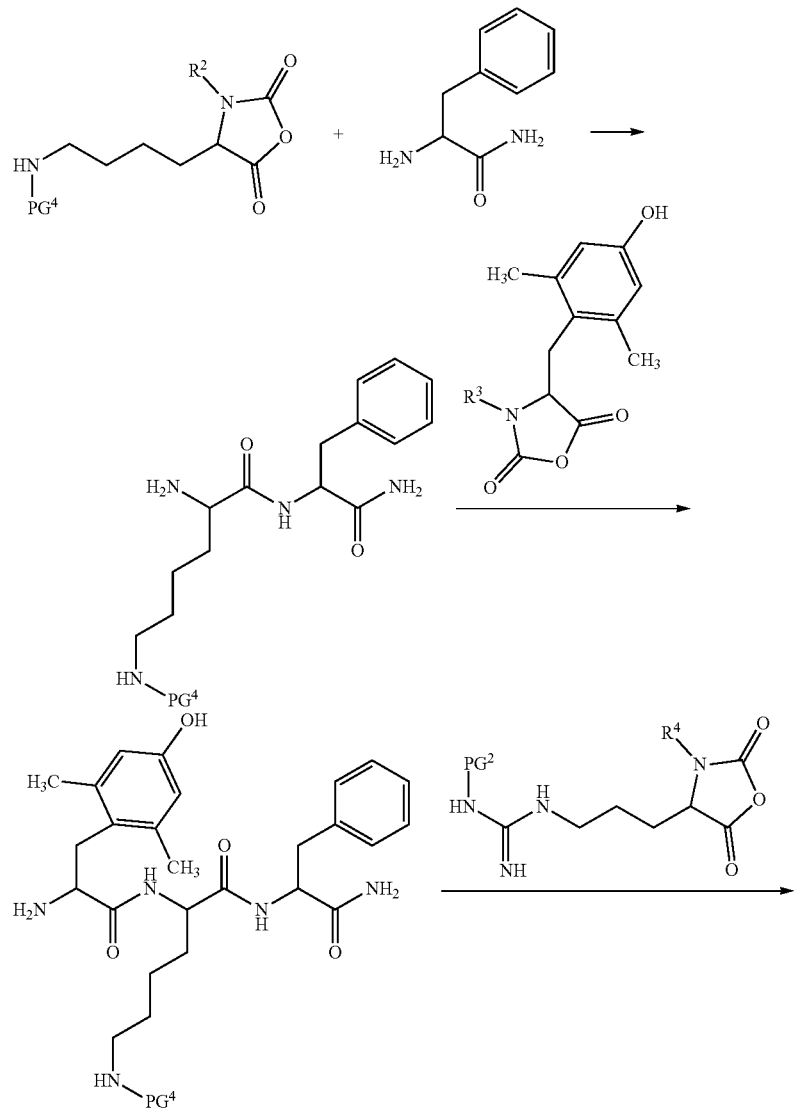

-continued

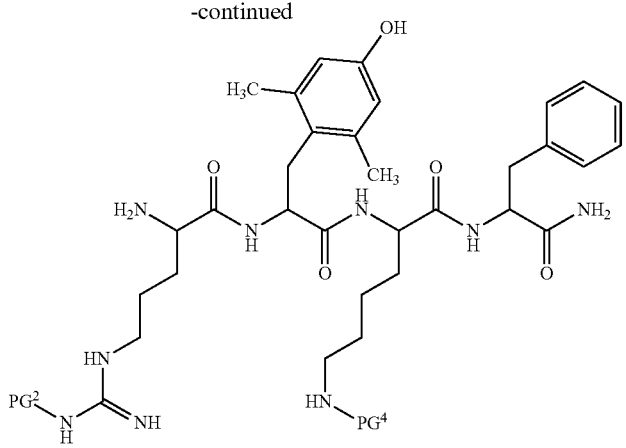

Accordingly, in other embodiments, the present invention provides a method of preparing compound 2, or a salt thereof, comprising:

combining compound 2a and compound 2b under conditions sufficient to produce compound 2, wherein:

compound 2 is represented by:

(compound 2)

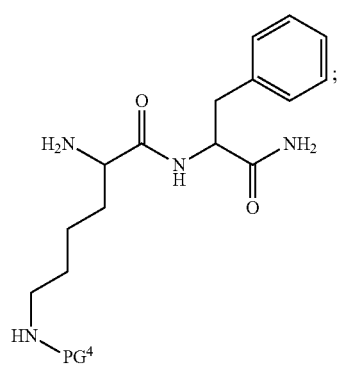

compound 2a is represented by:

(compound 2a)

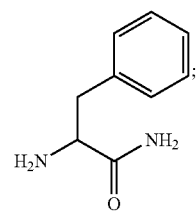

compound 2b is represented by:

(compound 2b)

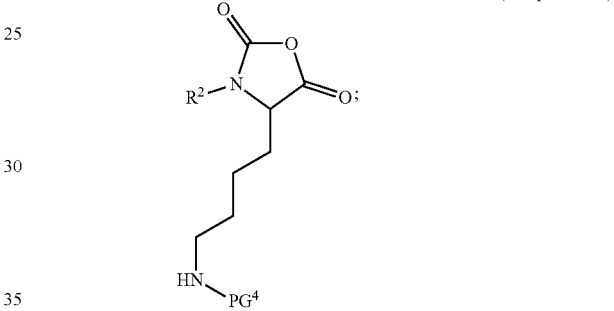

PG$^4$ represents an amino protecting group; and
R$^2$ represents H, alkyl, —C(O)O-alkyl, —C(O)O-aryl, —C(O)O-aralkyl, —C(O)O— heteroaryl, —C(O)O-heteroaralkyl, or aralkyl.

In certain embodiments, R$^2$ represents H.

In certain embodiments, PG$^4$ represents benzyloxycarbonyl (Cbz).

In certain embodiments, the method further comprises combining compound 2c and a phosgene equivalent reagent under conditions sufficient to produce compound 2b, wherein:

compound 2c is represented by:

(compound 2c)

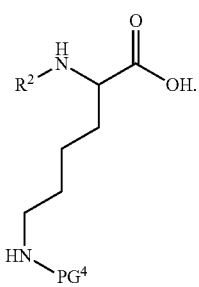

In certain embodiments, the phosgene equivalent reagent is selected from the group consisting of phosgene, diphosgene, triphosgene, carbonyl diimidazole, and disuccinimidyl carbonate.

In certain embodiments, the method further comprises combining compound 2 and compound 3a under conditions sufficient to produce compound 3, wherein:
compound 3 is represented by:

(compound 3)

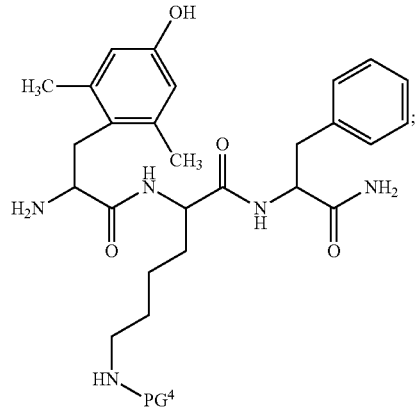

compound 3a is represented by:

(compound 3a)

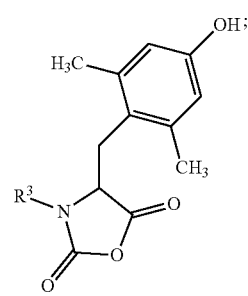

and
R³ represents H, alkyl, —C(O)O-alkyl, —C(O)O-aryl, —C(O)O-aralkyl, —C(O)O-heteroaryl, —C(O)O-heteroaralkyl, or aralkyl.

In certain embodiments, R³ represents H.

In certain embodiments, the method further comprises combining compound 3b and a phosgene equivalent reagent under conditions sufficient to produce compound 3a, wherein:
compound 3b is represented by:

(compound 3b)

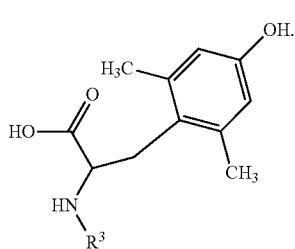

In certain embodiments, the phosgene equivalent reagent is selected from the group consisting of phosgene, diphosgene, triphosgene, carbonyl diimidazole, and disuccinimidyl carbonate.

In certain embodiments, the method further comprises combining compound 3 and compound 4a under conditions sufficient to produce compound 4, wherein:
compound 4 is represented by:

(compound 4)

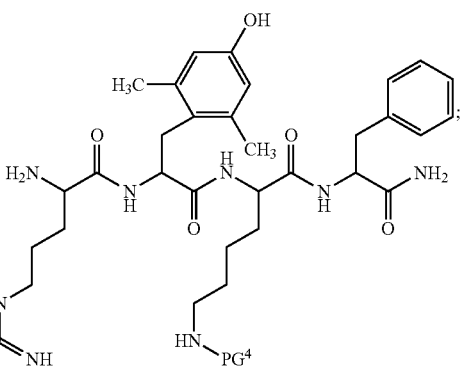

compound 4a is represented by:

(compound 4a)

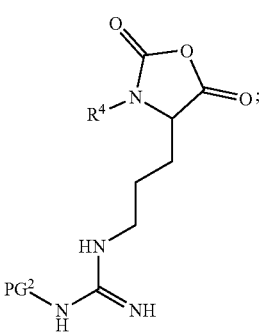

R⁴ represents H, alkyl, —C(O)O-alkyl, —C(O)O-aryl, —C(O)O-aralkyl, —C(O)O— heteroaryl, —C(O)O-heteroaralkyl, or aralkyl; and
PG² represents H or an amino protecting group.

In certain embodiments, R⁴ represents H.
In certain embodiments, PG² represents H.

In certain embodiments, the method further comprises combining compound 4b and a phosgene equivalent reagent under conditions sufficient to produce compound 4a, wherein:
compound 4b is represented by:

(compound 4b)

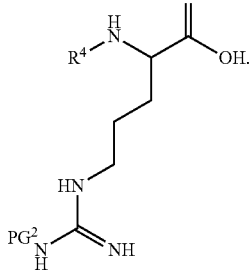

In certain embodiments, the phosgene equivalent reagent is selected from the group consisting of phosgene, diphosgene, triphosgene, carbonyl diimidazole, and disuccinimidyl carbonate.

In certain embodiments, compound 3 has the following structure:

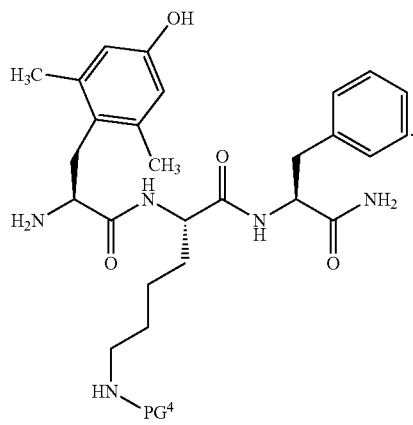

In certain embodiments, compound 4 has the following structure:

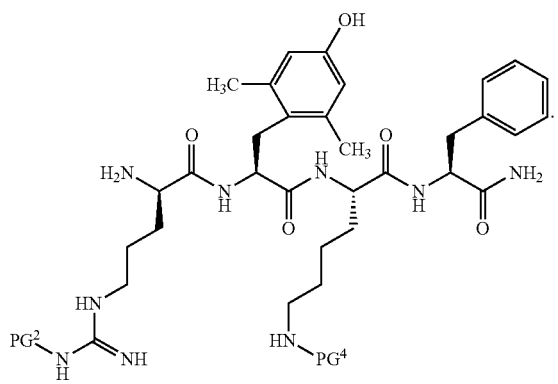

Elamipretide may also be synthesized via alternative linear convergent peptide synthesis routes, such as the route represented generally by Scheme 3. Protecting groups PG$^1$-PG$^5$ are defined herein.

Scheme 3: Alternative Linear Peptide Synthesis

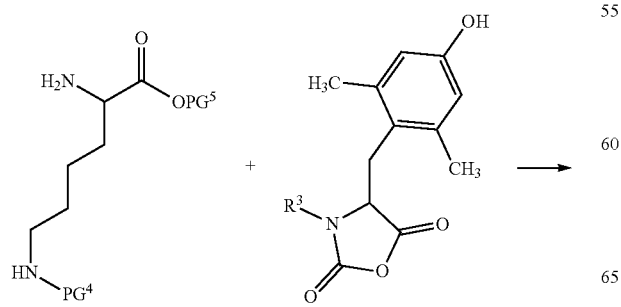

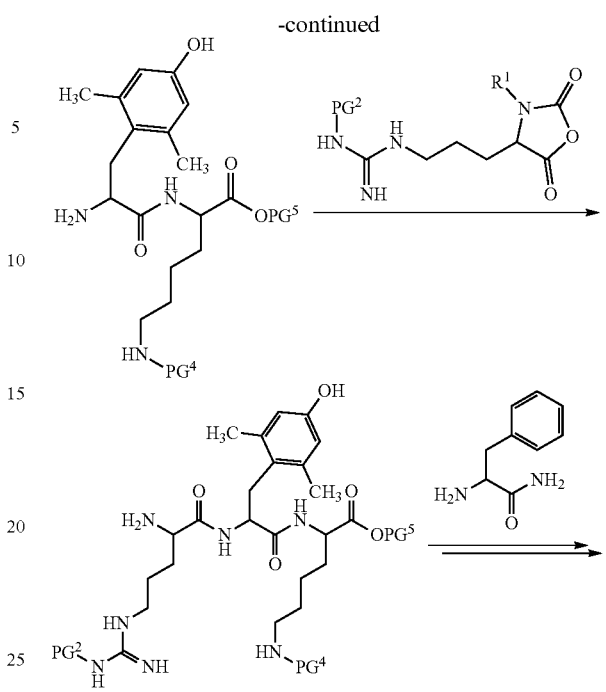

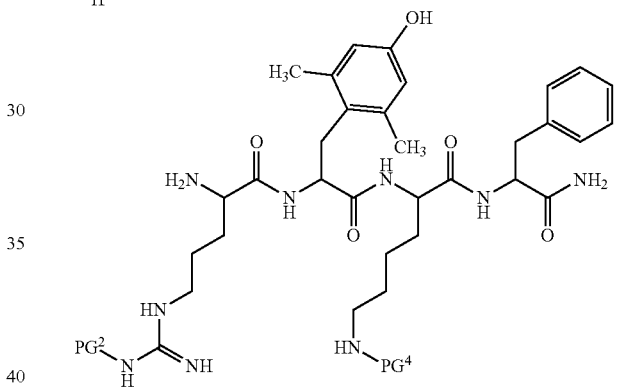

Accordingly, in certain embodiments, the invention provides a method of preparing compound 5, or a salt thereof, comprising:

combining compound 5a and compound 3a under conditions sufficient to produce compound 5, wherein:
compound 5 is represented by:

(compound 5)

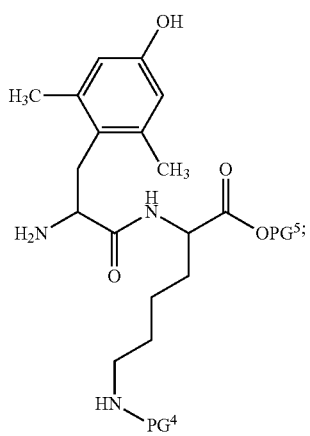

compound 5a is represented by:

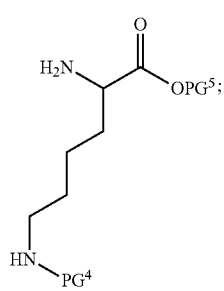
(compound 5a)

compound 3a is represented by:

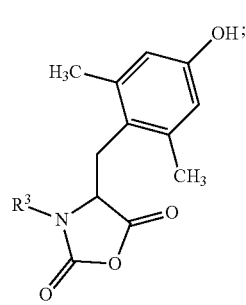
(compound 3a)

PG⁴ represents an amino protecting group;

PG⁵ represents alkyl, aryl, aralkyl, heteroaryl, heteroaralkyl, cycloalkyl, (cycloalkyl)alkyl, heterocycloalkyl, or (heterocycloalkyl)alkyl; and R³ represents H, alkyl, —C(O)O-alkyl, —C(O)O-aryl, —C(O)O-aralkyl, —C(O)O— heteroaryl, —C(O)O-heteroaralkyl, or aralkyl.

In certain embodiments, PG⁵ represents aralkyl or alkyl. Preferably, PG⁵ represents —CH₂Ph.

In certain embodiments, PG⁴ represents benzyloxycarbonyl (Cbz).

In certain embodiments, R³ represents H.

In certain embodiments, the method further comprises combining compound 3b and a phosgene equivalent reagent under conditions sufficient to produce compound 3a, wherein:

compound 3b is represented by:

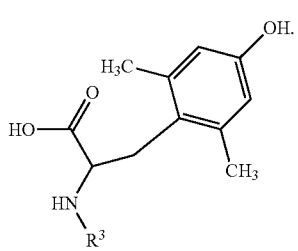
(compound 3b)

In certain embodiments, the phosgene equivalent reagent is selected from the group consisting of phosgene, diphosgene, triphosgene, carbonyl diimidazole, and disuccinimidyl carbonate.

In certain embodiments, the method further comprises combining compound 5 and compound 1b under conditions sufficient to produce compound 6, wherein:

compound 6 is represented by:

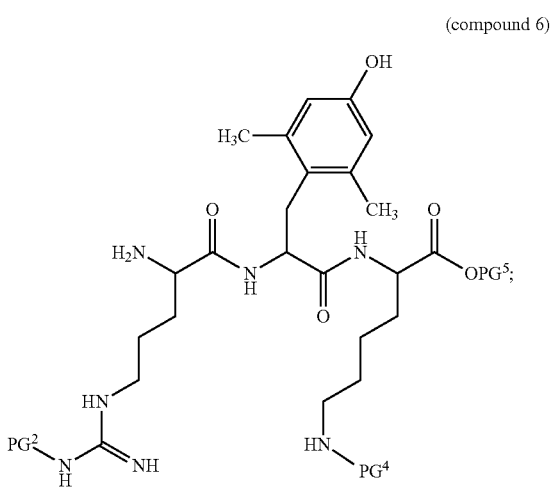
(compound 6)

compound 1b is represented by:

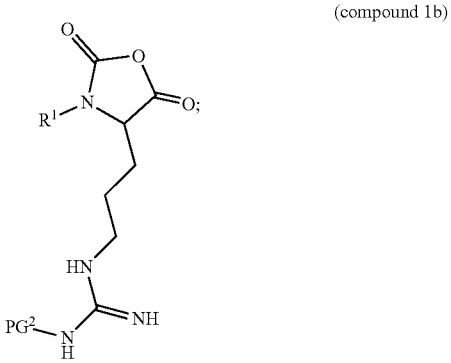
(compound 1b)

PG² represents H or an amino protecting group; and

R¹ represents H, alkyl, —C(O)O-alkyl, —C(O)O-aryl, —C(O)O-aralkyl, —C(O)O— heteroaryl, —C(O)O-heteroaralkyl, or aralkyl.

In some embodiments, PG² represents an amino protecting group. Alternatively, PG² may represent H.

In some embodiments, R¹ represents H.

In certain embodiments, the method further combining compound 1e and a phosgene equivalent reagent under conditions sufficient to produce compound 1b, wherein:

compound 1e is represented by:

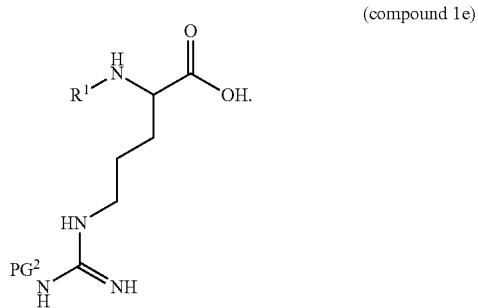
(compound 1e)

In certain embodiments, the phosgene equivalent reagent is selected from the group consisting of phosgene, diphosgene, triphosgene, carbonyl diimidazole, and disuccinimidyl carbonate.

In certain embodiments, compound 5 has the following structure:

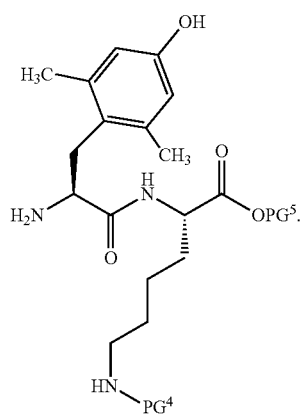

In certain embodiments compound 6 has the following structure:

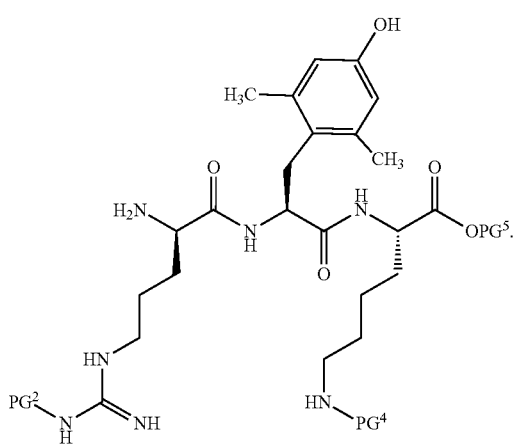

Elamipretide and other peptide intermediates produced by the methods of the invention can be collected or purified by a routine method, for example, chromatography, such as gel filtration chromatography, ion exchange column chromatography, affinity chromatography, reverse phase column chromatography, and HPLC, ammonium sulfate fractionation, ultrafiltration, and immunoadsorption.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

INCORPORATION BY REFERENCE

All U.S. patents and U.S. and PCT published patent applications mentioned in the description above are incorporated by reference herein in their entirety.

We claim:

1. A method of preparing compound 1, or a salt thereof, comprising:

combining compound 1a and compound 1b under conditions sufficient to produce compound 1, wherein:

compound 1 is represented by:

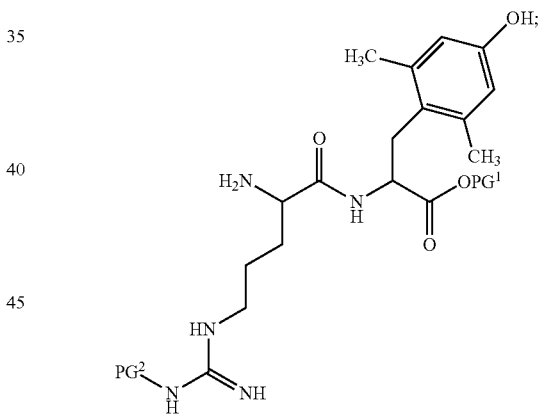

compound 1a is represented by:

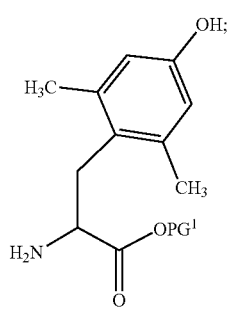

compound 1b is represented by:

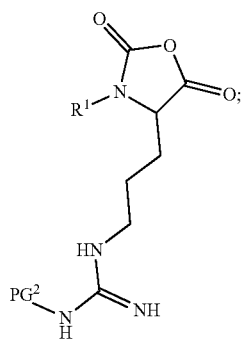

PG¹ represents alkyl, aryl, aralkyl, heteroaryl, heteroaralkyl, cycloalkyl, (cycloalkyl)alkyl, heterocycloalkyl, or (heterocycloalkyl)alkyl;

PG² represents H or an amino protecting group; and

R¹ represents H, alkyl, —C(O)O-alkyl, —C(O)O-aryl, —C(O)O-aralkyl, —C(O)O-heteroaryl, —C(O)O—heteroaralkyl, or aralkyl.

2. The method of claim 1, further comprising combining compound 1 with an amino protecting reagent represented by PG³-X, thereby forming compound 1c, wherein:

compound 1c is represented by:

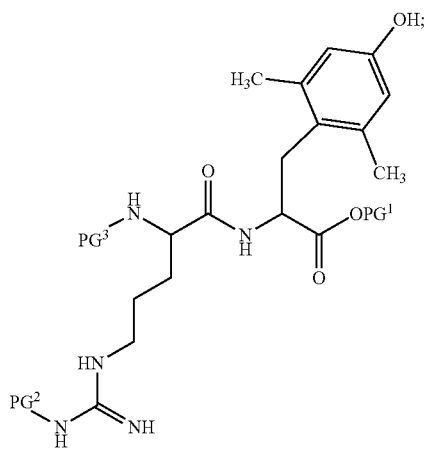

PG³ represents an amino protecting group; and

X represents a leaving group.

3. The method of claim 2, further comprising combining compound 1c and a deprotection reagent under conditions sufficient to form compound 1d, wherein:

compound 1d is represented by:

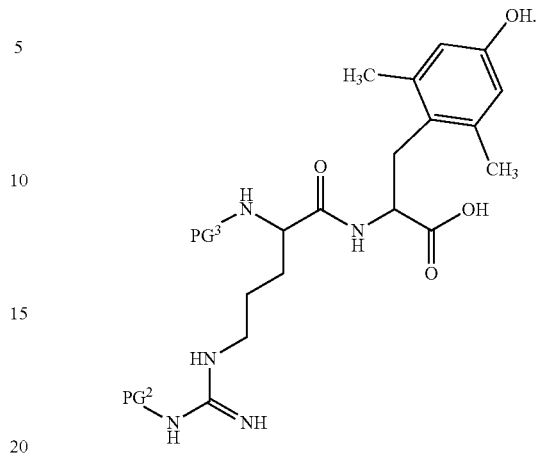

4. The method of claim 3, further comprising combining compound 1d and compound 2 under conditions sufficient to produce compound 10, wherein:

compound 10 is represented by:

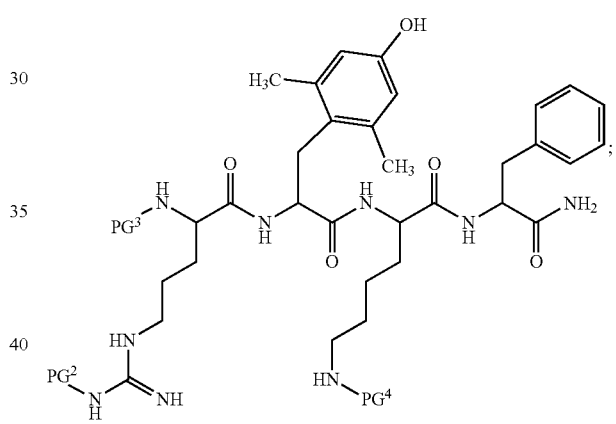

compound 2 is represented by:

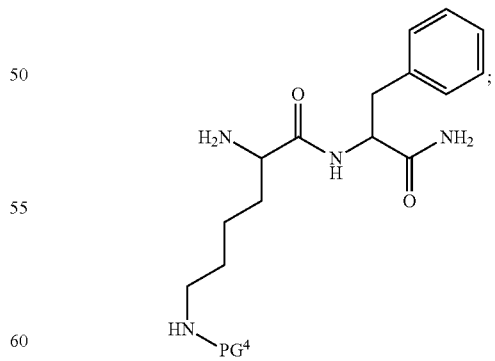

and

PG⁴ represents an amino protecting group.

5. The method of claim 4, wherein the conditions sufficient to produce compound 10 comprise a peptide coupling reagent.

6. The method of claim 1, further comprising combining compound 1e and a phosgene equivalent reagent under conditions sufficient to produce compound 1b, wherein:

compound 1e is represented by:

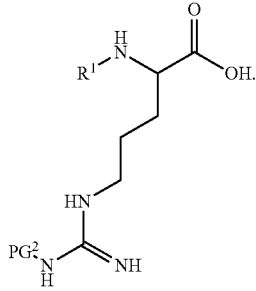

7. The method of claim 4, further comprising combining compound 2a and compound 2b under conditions sufficient to produce compound 2, wherein:

compound 2a is represented by:

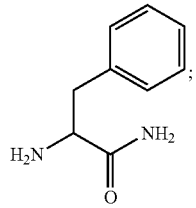

compound 2b is represented by:

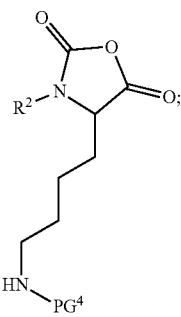

and

R² represents H, alkyl, —C(O)O-alkyl, —C(O)O-aryl, —C(O)O-aralkyl, —C(O)O-heteroaryl, —C(O)O-heteroaralkyl, or aralkyl.

8. The method of 7, further comprising combining compound 2c and a phosgene equivalent reagent under conditions sufficient to produce compound 2b, wherein:

compound 2c is represented by:

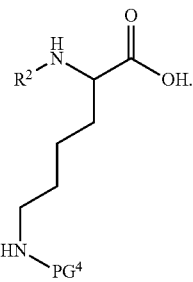

9. The method of claim 4, wherein compound 10 has the following structure:

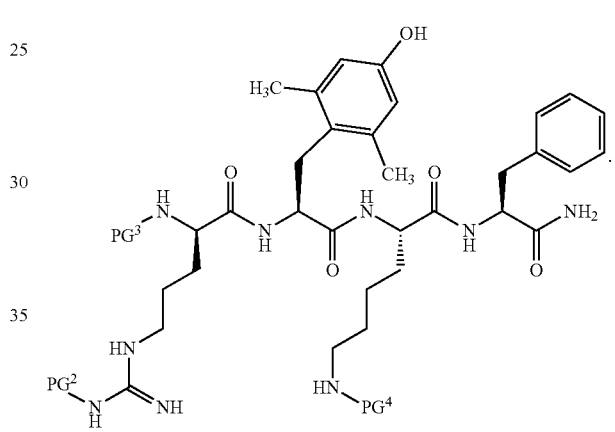

10. A method of preparing compound 2, or a salt thereof, comprising:

combining compound 2a and compound 2b under conditions sufficient to produce compound 2, wherein:

compound 2 is represented by:

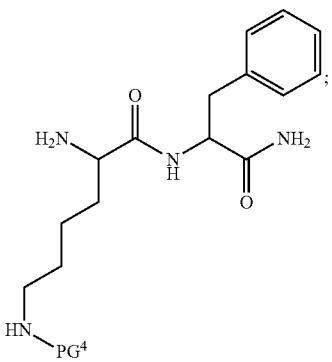

compound 2a is represented by:

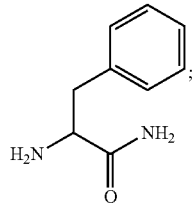

compound 2b is represented by:

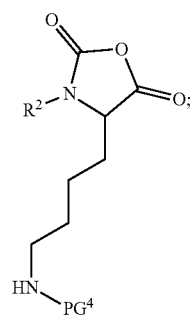

PG⁴ represents an amino protecting group; and
R² represents H, alkyl, —C(O)O-alkyl, —C(O)O-aryl, —C(O)O-aralkyl, —C(O)O-heteroaryl, —C(O)O— heteroaralkyl, or aralkyl.

11. The method of claim 10, further comprising combining compound 2c and a phosgene equivalent reagent under conditions sufficient to produce compound 2b, wherein:

compound 2c is represented by:

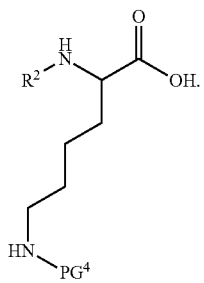

12. The method of claim 10, further comprising combining compound 2 and compound 1d under conditions sufficient to produce compound 10, wherein:

compound 10 is represented by:

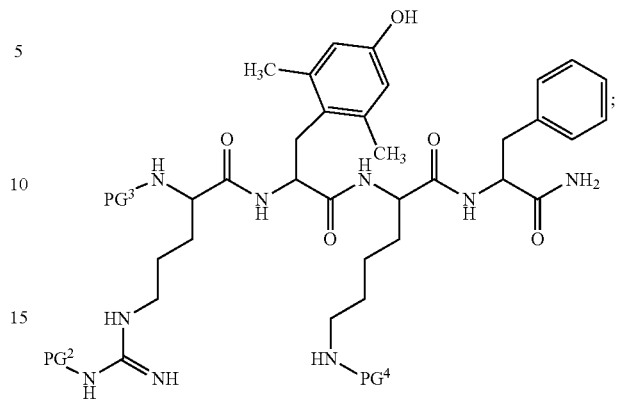

compound 1d is represented by:

PG² represents H or an amino protecting group; and
PG³ represents an amino protecting group.

13. The method of claim 10, further comprising combining compound 2 and compound 3a under conditions sufficient to produce compound 3, wherein:

compound 3 is represented by:

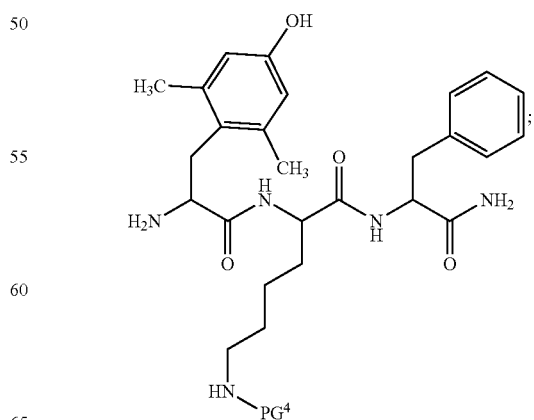

compound 3a is represented by:

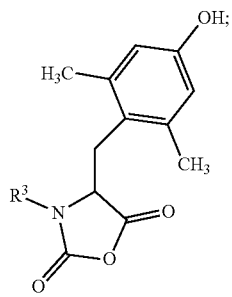

and

R³ represents H, alkyl, —C(O)O-alkyl, —C(O)O-aryl, —C(O)O-aralkyl, —C(O)O-heteroaryl, —C(O)O—heteroaralkyl, or aralkyl.

14. The method of claim 13, further comprising combining compound 3b and a phosgene equivalent reagent under conditions sufficient to produce compound 3a, wherein:

compound 3b is represented by:

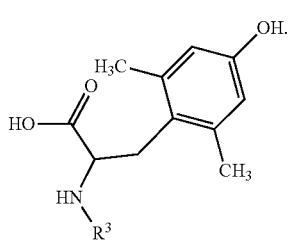

15. The method of claim 13, further comprising combining compound 3 and compound 4a under conditions sufficient to produce compound 4, wherein:

compound 4 is represented by:

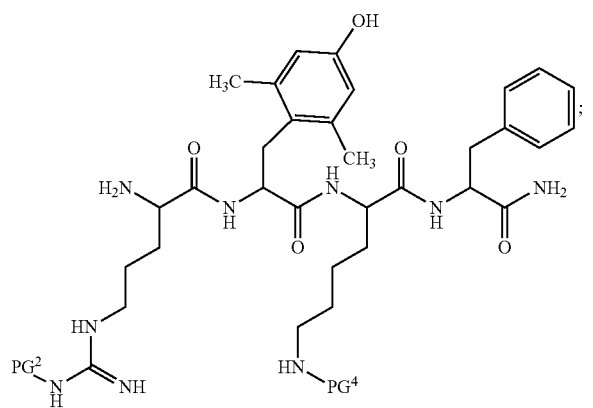

compound 4a is represented by:

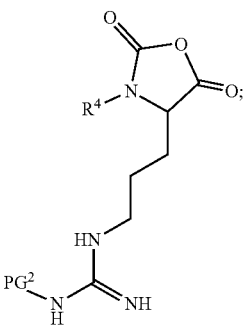

R⁴ represents H, alkyl, —C(O)O-alkyl, —C(O)O-aryl, —C(O)O-aralkyl, —C(O)O-heteroaryl, —C(O)O—heteroaralkyl, or aralkyl; and PG² represents H or an amino protecting group.

16. The method of claim 15, further comprising combining compound 4b and a phosgene equivalent reagent under conditions sufficient to produce compound 4a, wherein:

compound 4b is represented by:

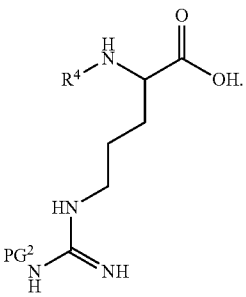

17. A method of preparing compound 5, or a salt thereof, comprising:

combining compound 5a and compound 3a under conditions sufficient to produce compound 5, wherein:

compound 5 is represented by:

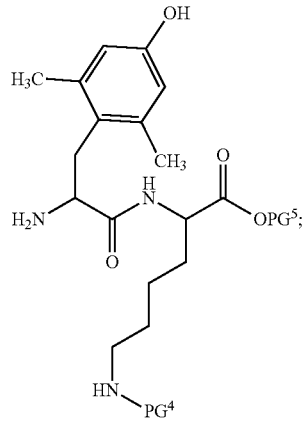

compound 5a is represented by:

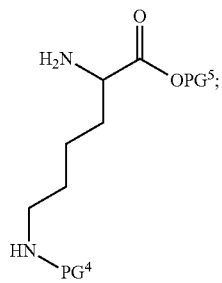

compound 3a is represented by:

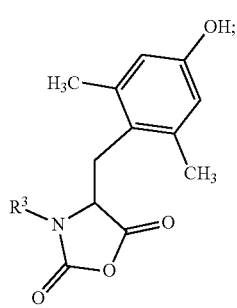

PG⁴ represents an amino protecting group;
PG⁵ represents alkyl, aryl, aralkyl, heteroaryl, heteroaralkyl, cycloalkyl, (cycloalkyl)alkyl, heterocycloalkyl, or (heterocycloalkyl)alkyl; and
R³ represents H, alkyl, —C(O)O-alkyl, —C(O)O-aryl, —C(O)O-aralkyl, —C(O)O-heteroaryl, —C(O)O—heteroaralkyl, or aralkyl.

18. The method of claim 17, further comprising combining compound 3b and a phosgene equivalent reagent under conditions sufficient to produce compound 3a, wherein:
compound 3b is represented by:

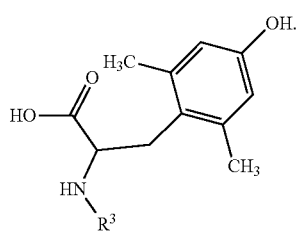

19. The method of claim 17, further comprising combining compound 5 and compound 1b under conditions sufficient to produce compound 6, wherein:

compound 6 is represented by:

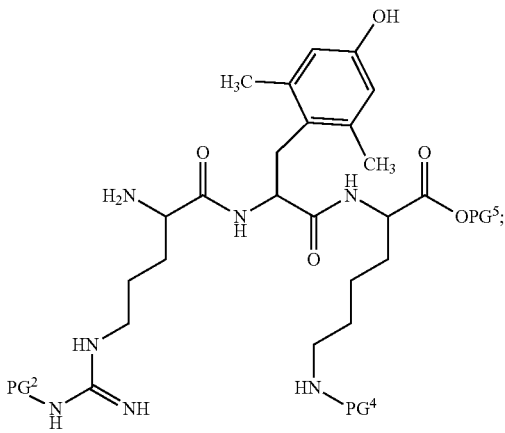

compound 1b is represented by:

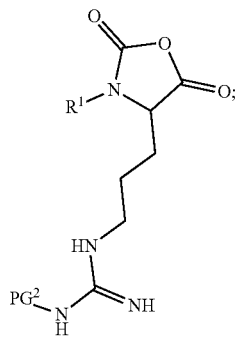

PG² represents H or an amino protecting group; and
R¹ represents H, alkyl, —C(O)O-alkyl, —C(O)O-aryl, —C(O)O-aralkyl, —C(O)O-heteroaryl, —C(O)O—heteroaralkyl, or aralkyl.

20. The method of claim 19, further comprising combining compound 1e and a phosgene equivalent reagent under conditions sufficient to produce compound 1b, wherein:
compound 1e is represented by:

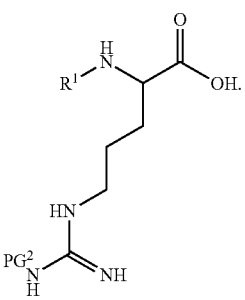

* * * * *